US00PP20381P3

(12) United States Plant Patent
Dozier, Jr. et al.

(10) Patent No.: US PP20,381 P3
(45) Date of Patent: Oct. 6, 2009

(54) CHESTNUT PLANT NAMED 'AU BUCK III'

(50) Latin Name: *Castanea mollissima*
Varietal Denomination: AU Buck III

(75) Inventors: W. Alfred Dozier, Jr., Opelika, AL (US); Joseph Daniel Norton, Auburn, AL (US); Curtis J. Hansen, Opelika, AL (US)

(73) Assignee: Auburn University, Auburn, AL (US)

( * ) Notice: Subject to any disclaimer, the term of this patent is extended or adjusted under 35 U.S.C. 154(b) by 0 days.

(21) Appl. No.: 12/012,110

(22) Filed: Jan. 30, 2008

(65) Prior Publication Data

US 2009/0193552 P1 Jul. 30, 2009

(51) Int. Cl.
*A01H 5/00* (2006.01)

(52) U.S. Cl. ..... Plt./152

(58) Field of Classification Search ..... Plt./152
See application file for complete search history.

(56) References Cited

OTHER PUBLICATIONS

Lin ye ke ji et al., "Forest Science & Technology", Jan. 1989, pp. 16-18, Baker Auxiliary Stacks SD1. L56, No. 2-1990.

Crane, H.L. et al., Nut Breeding, U.S. Department of Agriculture Yearbook, Jan. 1937, pp. 827-837.

Hemming, E. Sam, "Chinese Chestnut in Maryland", Jan. 1944, pp. 32-34, A.R. Northern Nut Growers Assoc.

Kim, Kap Duk et al., Studies on the Farmers Cultivating Chestnut Orchards in Korea and Its Financial Analysis, Jan. 1971, pp. 51-74, Bull. Seol. Nut. Univ.Fores., No. 8.

Snare, Lester, "Chestnuts Production", Jan. 1996, pp. 422-427, NSW Agriculture, Agfact H3.1.50., hhtp://www.rirdc.gov.au/pub/handbook/chestnuts.pdf.

Harris, Hubert et al., Three Chinese Chestnuts: Au-Cropper, Au-Leadder, and Au-Homestead—Their History and Production, Mar. 1980, pp. 3-8, Agricultural Experiment Station Auburn University Circular 247.

*Primary Examiner*—Annette H Para
(74) *Attorney, Agent, or Firm*—Haverstock & Owens LLP

(57) ABSTRACT

'AU Buck III' is a new and distinct Chinese chestnut cultivar that is blight resistant, precocious and an annual bearer. It produces a medium to heavy crop load each year and a medium sized nut. Nut drop begins about September 25 and continues for a 4–5 week period. A large percentage of the nuts drop during the first three weeks of the period that nuts drop from this cultivar. 'AU Buck III' is a small to medium sized tree that is round in shape with low, dense, and spreading branches that was 6.71 meters tall, with a canopy covering an area of 41.85 square meters at 20 years old. 'AU Buck III' is the third cultivar to mature and drop nuts in a series of four Chinese chestnut cultivars that will provide for a continuous nut drop of a high energy wildlife food source from late August through mid-to-late November.

3 Drawing Sheets

Latin name of the genus and species of the plant claimed: *Castanea mollissima* Blume.

Variety denomination: 'AU Buck III'.

BACKGROUND OF THE INVENTION

A Chinese chestnut planting was established at Auburn University, Auburn, Ala., from nuts collected in China. The planting was established on the United States Department of Agriculture Horticulture Farm which in later years became the Mainstation Horticulture Farm. Precocious and prolific-bearing, blight resistant seedlings were selected for nut appearance, size and quality. Each generation of seedlings were the product of controlled mass pollination from the most promising seedlings selected from the previous generation. 'AU Cropper', 'AU Leader' and 'AU Homestead' were released from a second generation of approximately 2000seedlings. A planting of third generation seedlings from controlled mass pollination of 'AU Leader', 'AU Homestead' and 'AU Cropper' was established at the Auburn University Piedmont Substation at Camp Hill, Ala.

SUMMARY OF THE INVENTION

'AU Buck III' is from a sister line to 'AU Leader,' 'AU Homestead' and 'AU Cropper'.

The present invention relates to a new and distinct Chinese chestnut cultivar that is blight resistant, precocious, produces a heavy crop annually, average nut size is medium (10.9 g), and begins nut drop about September 25 and continues for a 4–5 week period. A high percentage of the nuts produced drop during the first three weeks of the period that nuts drop from this cultivar. Nut drop from 'AU Buck III' begins about 2 weeks after nut drop from 'AU Buck II' begins. The medium sized nut is an excellent food source for wildlife such as deer and squirrels. The 20-year old tree of 'AU Buck III' is a small to medium sized tree in height that is 6.71 meters tall with a canopy of 7.29 meters wide and covers a canopy area of 41.85 square meters. The 'AU Buck III' tree has produced a heavy crop load each season for tree size and produced 20.3 kg (44.8 lbs) in 2006.

'AU Buck III' is the third cultivar to mature and drop nuts in a series of four Chinese chestnut cultivars that will provide for a continues nut drop of a high energy wildlife food source from late August through mid-to-late November. 'AU Buck I', 'AU Buck II' and 'AU Buck IV' are the other three cultivars, which are disclosed in U.S. patent application No. 12/012,091, filed on Jan. 30, 2008, and entitled "Chestnut Plant Named 'AU Buck I'", U.S. patent application No. 12/012,025, filed on Jan. 30, 2008, and entitled "Chestnut Plant Named 'AU Buck II'" and U.S. patent application No.

12/012,112, filed on Jan. 30, 2008, and entitled "Chestnut Plant Named 'AU Buck IV'", which are hereby incorporated by reference.

The new cultivar is able to be asexually reproduced by budding and grafting onto a seedling Chinese chestnut rootstock. The unique characteristics come true to form and are established and transmitted through asexual propagation.

DETAILED BOTANICAL DESCRIPTION

Figure 1:
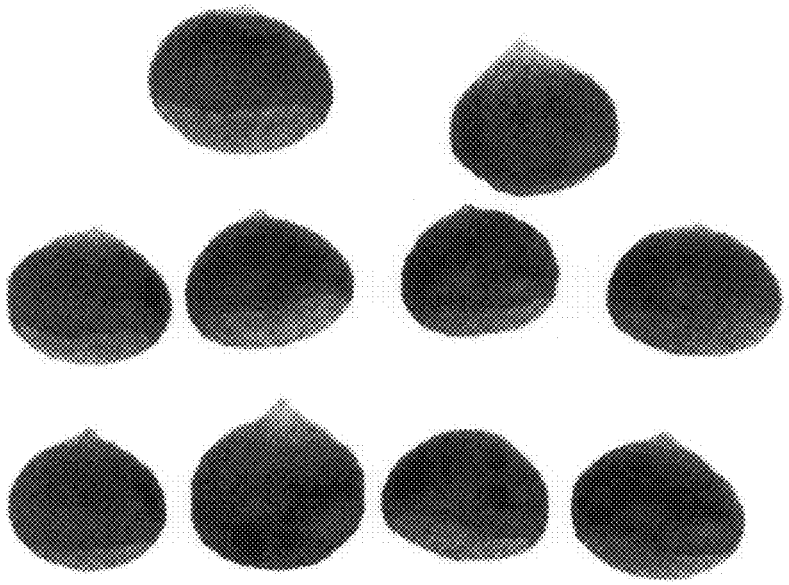
FIG. 1 is a photograph of nuts of the 'AU Buck III' cultivar.
Figure 2:
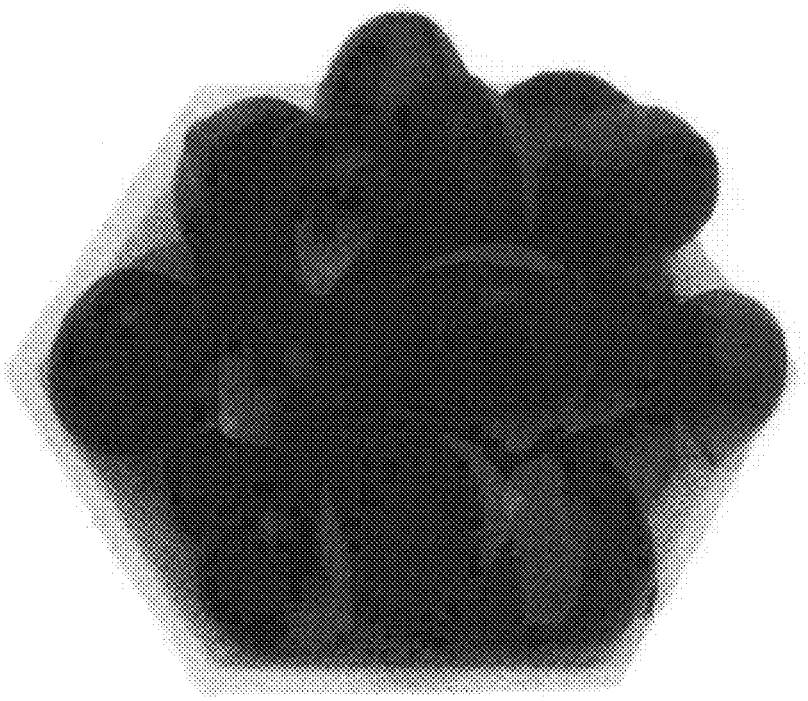
FIG. 2 is a photograph of nuts of the 'AU Buck III' cultivar.
Figure 3:
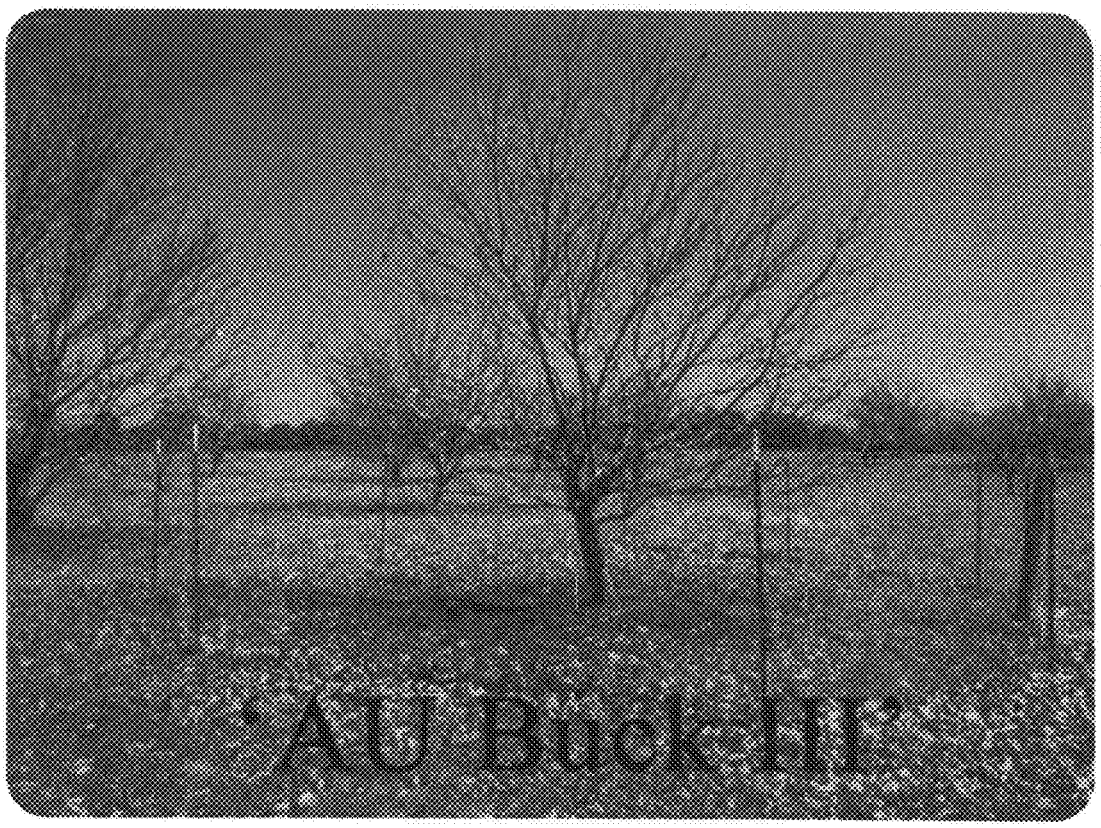
FIG. 3 is a photograph of a tree of the 'AU Buck III' cultivar.

The Chinese chestnut, *Castanea mollissima* Blume, is a cold hardy temperate zone species native to China. It can be grown between 30° and 50° latitudes. The Chinese chestnut is resistant to chestnut blight fungus *Cryphonectria parasitica*. Generally, Chinese chestnuts are grown on a wide range of soils, but well-drained, deep and fertile soils are considered the best. Soils should be slightly acidic with pH 5.6–6.5. The name *mollissima* means soft hair and this species is recognized by dense hair on young leaves and downy yellow terminal parts of the shoots in winter. The leaf blade is thicker, and, in general, mature leaves are broader than those of other species. The nuts have a small scar or hilum. The pellicle or thin membranous skin on the nuts is thin and peels readily from the kernel. The trees are a spreading type and long-lived with a round top. The trees have bark with furrows and buds with 3–4 scales and leaves are 2 ranked, serrated with numerous parallel veins.

Chestnuts are monoecious and staminate flowers appear on erect cylindrical catkins with 10–20 stamens and 6-parted calyx. Pistillate flowers are borne on lower part of the upper staminate catkins and rarely on separate catkins usually 3 in a prickly symmetrical involucre with 7–9 styles and a 6-celled ovary. Nuts are small, brown with a pale scar at the base. Generally, 1–3 nuts per involucre or bur are present.

'AU Buck III' is a small to medium sized tree that is round in shape with low, dense, and spreading branches. The 20-year old tree is 6.71 meters (22.0 feet) tall, with a trunk diameter at breast height of 22.6 cm (8.90 inches). The canopy is 7.29 meters (23.90 feet) wide and covers an area of 41.85 square meters (450.48 square feet). The average nut weight is 10.9 g, average nut length is 28.4 mm (1.12 inches) and the average nut width is 30.4 cm (1.30 inches). The nuts start dropping about September 25 and continue to drop for a 4 to 5 week period. A high percent of the nuts produced drop during the first three weeks of the period that nuts drop from this cultivar. Nut drop from 'AU Buck III' begins about 2 weeks after nut drop from 'AU Buck II' begins. 'AU Buck III' is prolific and fruits annually.

In the planting at the Piedmont Substation, Camp Hill, Ala., accurate yields could not be obtained due to extremely heavy wildlife (deer and turkey) feeding. Therefore, the trees were rated for crop load each year. 'AU Buck III' has been a producer of a medium to large crop load each season. In the fall of 2006, individual trees were caged with 6 foot (1.83 meters) tall chicken wire prior to nut drop to exclude wildlife and nuts were picked up daily from the beginning through completion of nut drop. The 20-year old 'AU Buck III' tree produced 20.3 kg (44.8 pounds) of nuts in 2006. This yield is similar to reported yields of similar aged trees.

The table below illustrates the specific differences between the 'AU BUCK III' cultivar and the 'REVIVAL' cultivar.

The botanical details of this new and distinctive variety of chestnut tree - with color definitions (except those in common color terms) referenced to Royal Horticultural Society's Colour Chart (RHS) and color was also determined using an electronic spectrophotometer to determine hue angle and Chroma (spectrophotometer model CM-2002; Minolta Camera Co., Japan).

'AU BUCK III' CHESTNUT

Tree:

Size (at maturity) - small - twenty year old original tree is 6.71 meters tall with a canopy width of 7.29 meters and a canopy area of 41.85 sq. meters
Tree shape is round.
Vigor - very vigorous Trunk:

Form - upright with branches low and dense
Texture - relatively smooth
Color of bark - brown RHS N200A, Chroma C* 11.29, hue angle 80.74

Branches:

Form - spreading
Texture - relatively smooth
Lenticels - few, small
Branching habit - low and dense
Color - new wood: brown, RHS 200C, Chroma C* 16.06, hue angle 68.53, mature wood: grey-brown RHS N199A Chroma C* 13.18, hue angle 88.29

Foliage:

Quantity - abundant
Density - dense

Leaves:

Size - large. Length (cm) 19.3 (16.1-22.1) [20]
width (cm) 7.7 (5.0-9.5) [20]
leaf ratio 2.6 (2.2-3.4) [20]
Shape - oblong-elliptic
leaf tip - acute to occasionally acuminate
leaf base - cuneate to rounded; equal, rarely oblique
Thickness - thick. Leaf venation 1° pinnate: 2° parallel, strongly prominent abaxially
Texture - strongly coriaceous
Margin - coarsely serrate; teeth spreading, ascending
Petiole - length 1.4 cm (0.9-2.1) [20]
Petiole pubescence - mixed stellate and simple hairs
Color- adaxial surface, glabrous blade; simple and stellate hairs on main veins medium to dark green; very shiny, RHS 147A, Chroma C* 16.23, hue angle 117.35
abaxial surface, densely stellate hairs mixed with occasional long straight hairs on blade, long simple hairs on main veins, RHS 147B, Chroma C* 21.68, hue angle 103.78

Bloom:

Amount of bloom - heavy
Color - at anthesis, 161D greyed-yellow group, 157D green-white group, 155C white group
Blooming period - mid-May. After foliation in April.
Age at which tree starts flowering - early, 2-3 years after graft replacement.
Male flower - Catkin length (cm) - 14.0 (9.6-19.8) [10]
Male flower - stamen number per catkin - 10.8 (8.13) [10]
Female flower - flower number per bur - 3
Female flower - style number per flower 7.7 (7-8) [3]

Crop:

Bearing - regular annual bearer
Productivity - prolific
Ripening period - long, nuts begin dropping about September 25 and continues for a 4-5 week period.
Distribution of nuts on tree - well distributed, fruits on terminals with 2-4 burs per terminal.
Tenacity - burs crack while on tree and nuts release and drop from bur.

-continued

Hull:

Description - spiny round bur
Size - 2.34-2.56" in diameter
Number of nuts - 2-3 per bur
Dehiscence - splits easily when still on tree
Color - yellow-green at dehiscence, RHS N144C Nut:

Size -medium; average size- 1.12" × 1.30" × 0.71".
Average weight - 10.9 grams
42 (36-46) nuts per pound.
Form - flattened on 1 side, occ. 2, hemispheric on the other side,
Blossom end - small obtuse tip
Basal end - broadly rounded
Color - brown, lustrous RHS 200B, Chroma C* 11.58, hue angle 36.17
Pubescence- mixed long and short, fine, white hairs densely covering ¼ of the distal end, otherwise very sparse to glabrous elsewhere
Shell - thin
Hardness of shell - relatively hard, yet not rigid
Texture of shell - smooth
Percentage of kernel to nut - very high-90-95%

Kernel:

Size - almost as large as nut size
Form - same as nut shape
Pellicle - thin
Flavor - excellent, very sweet
Color - straw color, RHS 152D, Chroma C* 48.19, hue angle 81.90
Resistance to insects: no unusual susceptibilities noted
Resistance to disease: no susceptibilities to disease noted
The chestnut tree and its nuts herein described may vary in slight detail due to climatic and soil conditions under which the variety may be grown; the present description being of the variety as grown in Camp Hill, Ala.

The botanical details of this variety of chestnut tree - with color definitions (except those in common color terms) referenced to Maerz and Paul Dictionary of Color - are as follows:

'REVIVAL'

Tree:

Size (at maturity) - large
Vigor - very vigorous

Trunk:

Form - upright with branches spreading in upper reaches of tree.
Texture - relatively smooth
Color of bark - Silvergray (13-A-1)

Branches:

Form - strong
Texture - relatively smooth
Lenticels - few, small
Branching habit - spreading in upper region of tree
Color - new wood: reddish brown and glossy, mature wood: silver gray Foliage:

Quantity - abundant
Density - dense

Leaves:

Size - large. Average length - 5-7" (including petiole).
Average width - 2"
Shape - oblong with acute tip and rounded base
Thickness - thick
Texture - smooth
Margin - dentate
Petiole - length: medium. Thickness: medium.
Color - Top side - glossy dark green (22-L-12).
Under side - lighter green (21-D-7).

-continued

Bloom:

Amount of bloom - heavy
Color - cream white (17-B-1)
Blooming period - late. After leaf out in April
Age at which tree starts flowering - early; 2-3 years years after graft replacement.

Crop:

Bearing - regular (yearly) bearer
Productivity - prolific
Ripening period - short. September 15-October 1.
Distribution of nuts on tree - well distributed
Tenacity - burrs crack while on tree and nuts easily release, many falling by themselves Hull:

Description - spiny, round burr
Size - 3-4" in diameter
Number of nuts - 2-3 per burr
Dehiscence - splits easily when still on tree. Some entire burrs split and fall to ground
Color - brown (15-A-8)

Nut:

Size-large. Average size - 1⅛" × 1⅛" × 1" thick,
Average weight - 24-32 nuts per pound
Form - broad and ovoid on one side, flat on other side
Blossom end - pointed tip
Basal end - flattened
Color - India Red (7-L-6).
Shell - thin
Hardness of shell - relatively hard, yet not rigid
Texture of shell - smooth
Percentage of kernel to nut - very high (95%)

Kernel:

Size - almost as large as nut size
Form - same as nut shape
Pellicle - thin
Flavor - excellent. Very sweet.
Color - Oyster white (10-B-1)
Resistance to insects: no unusual susceptibilities noted
Resistance to disease: very high inherent resistance to chestnut bark fungus (*Endothia parastica*), no other susceptibilities to any other disease
The chestnut tree and its nuts herein described may vary in slight detail due to climatic and soil conditions under which the variety may be grown; the present description being of the variety as grown in Alachua, Fla.

'AU Buck III' is different from 'AU Gobbler I' in several ways. For example, the size of the trees, the trunk forms and colors, the branches, the leaves, the crop and the nuts have differences. Specifically, the 'AU Buck III' tree is shorter with a canopy area smaller than the 'AU Gobbler I' tree. The 'AU Buck III' branches are spreading and brown (new) or grey-brown (mature); whereas, the 'AU Gobbler I' branches are upright and brown (new) or greyed-green (mature). The leaves differ in size, petiole and color. The ripening period for the 'AU Buck III' is around September 25 and continues for a 4–5 week period, but the 'AU Gobbler I' ripening period is around August 25 and continues for 4–5 weeks. The average weight of the nuts of 'AU Buck III' is 10.9 grams versus 7.7 grams for 'AU Gobbler I'. Furthermore, 'AU Buck III' has roughly 42 nuts per pound, and 'AU Gobbler I' has roughly 59 nuts per pound.

'AU Buck III' is different from 'AU Gobbler II' in several ways. For example, the trees, the trunk colors, the branch colors, the leaves, the crop and the nuts have differences. Specifically, the 'AU Buck III' tree is shorter with a canopy width and canopy area smaller than the 'AU Gobbler II' tree. The 'AU Buck III' branches are brown (new) or grey-brown (mature); whereas, the 'AU Gobbler II' branches are brown (new) or greyed-green (mature). The leaves differ in size, shape and color. The ripening period for the 'AU Buck III' is around September 25 and continues for a 4–5 week period, but the 'AU Gobbler II' ripening period is around September 5 and continues for 4–5 weeks. The average weight of the nuts of 'AU Buck III' is 10.9 grams versus 5.7 grams for 'AU Gobbler II'. Furthermore, 'AU Buck III' has roughly 42 nuts per pound, and 'AU Gobbler II' has roughly 65–101 nuts per pound.

'AU Buck III' is different from 'AU Premier' in several ways. For example, the trees, the trunk colors, the branch colors, the leaves, the crop and the nuts have differences. Specifically, the 'AU Buck III' tree is taller with a canopy width and canopy area larger than the 'AU Premier' tree. The 'AU Buck III' has a brown trunk, and the 'AU Premier' has a greyed-green trunk. The 'AU Buck III' branches are brown (new) or grey-brown (mature); whereas, the 'AU Premier' branches are brown (new) or greyed-green (mature). The leaves differ in size, shape, thickness, texture, petiole and color. The ripening period for the 'AU Buck III' is around September 25, and the 'AU Premier' ripening period is early September through mid-November. The average weight of the nuts of 'AU Buck III' is 10.9 grams versus 1.26 grams for 'AU Premier'. Furthermore, 'AU Buck III' has roughly 42 nuts per pound, and 'AU Premier' has roughly 360.3 nuts per pound.

'AU Buck III' is different from 'AU Encore' in several ways. For example, the trees, the trunk colors, the branch colors, the leaves, the crop and the nuts have differences. Specifically, the 'AU Buck III' tree is taller with a canopy width larger than the 'AU Encore' tree. The 'AU Buck III' has a brown trunk, and the 'AU Encore' has a greyed-green trunk. The 'AU Buck III' branches are brown (new) or grey-brown (mature); whereas, the 'AU Encore' branches are brown (new) or greyed-green (mature). The leaves differ in size, thickness, texture, margin, petiole and color. The ripening period for the 'AU Buck III' is around September 25, but the 'AU Encore' ripening period is late September through late November. The average weight of the nuts of 'AU Buck III' is 10.9 grams versus 2.4 grams for 'AU Encore'. Furthermore, 'AU Buck III' has roughly 42 nuts per pound, and 'AU Encore' has roughly 189.2 nuts per pound.

What is claimed is:

1. A new and distinct cultivar of the species *Castanea mollissima* Blume named 'AU Buck III' as described and illustrated herein.

* * * * *

'AU Buck III'

'AU Buck III'

UNITED STATES PATENT AND TRADEMARK OFFICE

CERTIFICATE OF CORRECTION

PATENT NO. : PP 20,381 P3
APPLICATION NO. : 12/012110
DATED : October 6, 2009
INVENTOR(S) : Dozier, Jr. et al.

It is certified that error appears in the above-identified patent and that said Letters Patent is hereby corrected as shown below:

At column 4, line 38, please change "2° parallel" to "2° ± parallel" so that the line reads -- Thickness - thick. Leave venation 1° pinnate: 2° ± parallel, strongly prominent abaxially. --

Signed and Sealed this

Twelfth Day of January, 2010

David J. Kappos

David J. Kappos
*Director of the United States Patent and Trademark Office*